US00PP13198P3

(12) United States Plant Patent
Cain

(10) Patent No.: US PP13,198 P3
(45) Date of Patent: Nov. 12, 2002

(54) GRAPEVINE CV. 'SUGRATWENTYTWO'

(75) Inventor: David W. Cain, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 13 days.

(21) Appl. No.: 09/770,719

(22) Filed: Jan. 25, 2001

(65) Prior Publication Data

US 2002/0138885 P1 Sep. 26, 2002

(51) Int. Cl.[7] ..... A01H 5/00

(52) U.S. Cl. ..... Plt./207

(58) Field of Search ..... Plt./207

*Primary Examiner*—Bruce R. Campell
*Assistant Examiner*—Michelle Kizilkaya
(74) *Attorney, Agent, or Firm*—Knobbe, Martens, Olson & Bear

(57) ABSTRACT

A new and distinct grapevine variety characterized by white seedless berries of oblong shape and medium size. The new variety ripens very late, and is extremely productive when pruned to short spurs.

1 Drawing Sheet

BACKGROUND AND SUMMARY OF THE INVENTION

This invention relates to the discovery and asexual propagation of a new variety of grapevine, *Vitis vinifera* cv. 'Sugratwentytwo'. The new variety was first hybridized by David W. Cain in Wasco, Kern County, Calif., the variety being originated by controlled hybridization and subsequent embryo rescue of abortive seed traces. The new variety is characterized by white, medium sized seedless berries that are crisp and are oblong in shape. The new variety produces larger berries in response to gibberellic acid application, and is extremely productive when pruned to short spurs.

The seed parent is 'Sun World Breeding Selection 89152-064-236' (unpatented) and the pollen parent is 'Sun World Breeding Selection 89134-202-189' (unpatented). The parent varieties were first crossed in May, 1993, with the date of first flowering being May, 1995. The new 'Sugratwentytwo' variety was first asexually propagated by David W. Cain in December, 1995 in Wasco, Kern County, Calif., using hardwood cuttings.

The new grapevine variety cv. 'Sugratwentytwo' resembles its seed parent '89152-064-236' in outward appearance, but differs by producing berries with superior eating quality, containing higher sugar and lower acid content than in the maternal parent. 'Sugratwentytwo' is distinguished from the pollen parent, '89134-202-189' by being more elongated, in addition to exhibiting better harvesting and shipping characteristics due to its stronger, more lignified peduncle, rachis, pedicel and torus that function to attach the berries more strongly to the cluster.

The new 'Sugratwentytwo' is distinguished from other commonly grown grapes such as the 'Autumn Seedless' (unpatented) and the 'Thompson Seedless' (unpatented) varieties. The 'Sugratwentytwo' most nearly resembles the 'Autumn Seedless' variety, but is distinguished from the 'Autumn Seedless' variety by producing crisp berries that have a creamy yellow green color. The 'Autumn Seedless' variety, in contrast, produces berries of less commercially acceptable darker green color that turn pink when exposed to direct sunlight. Moreover, while the yields of the 'Autumn Seedless' variety are often low, the new 'Sugratwentytwo' variety possesses a fruitful vine that is more capable of producing commercially acceptable yields.

'Sugratwentytwo' bears a slight resemblance to the 'Thompson Seedless' variety but is distinguished from the 'Thompson Seedless' variety by several important characteristics. The new variety 'Sugratwentytwo' produces berries that are more crisp and naturally larger than the 'Thompson Seedless' variety. 'Sugratwentytwo' berries have a stronger attachment to the cluster, and are more resistant to adverse weather conditions than the 'Thompson Seedless' variety. The vestigial seeds of 'Sugratwentytwo' are slightly larger than the vestigial seeds of the 'Thompson Seedless' variety. Additionally, 'Sugratwentytwo' berries can be allowed to stay on the vine much later, as they ripen approximately 60 days later than the 'Thompson Seedless' variety.

The new 'Sugratwentytwo' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
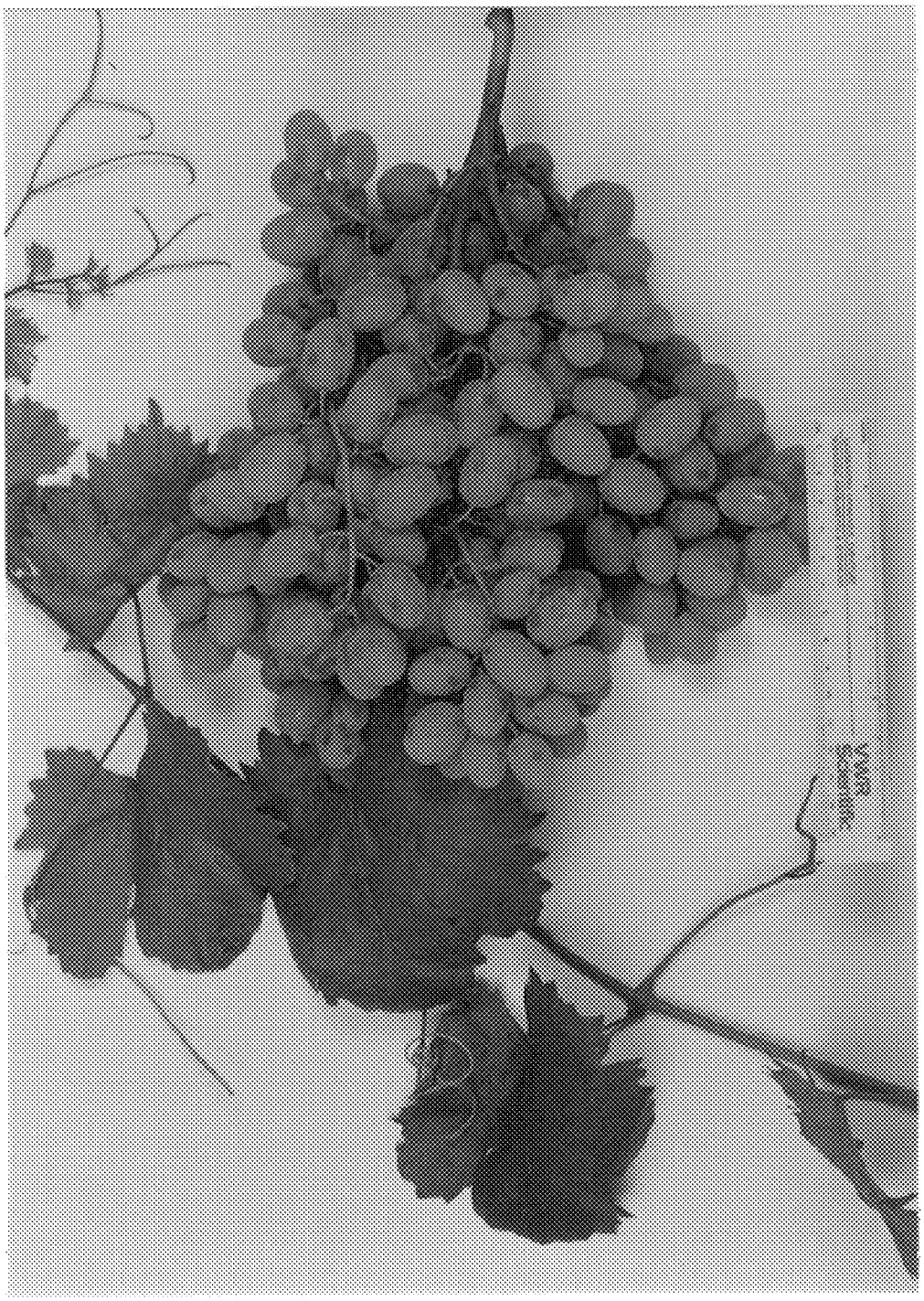

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwentytwo' plants grown in the vicinity of Wasco, Kern County, Calif., during 2000, and is believed to apply to plants of the variety grown under similar conditions of soil and climate elsewhere:

VINE

General:
- *Size.*—Large.
- *Vigor.*—Vigorous.
- *Density of foliage.*—Medium.
- *Productivity.*—Productive.
- *Root stock.*—Own root.

Trunk:
- *Shape.*—Medium.
- *Straps.*—Short, split.
- *Surface texture.*—Shaggy.
- *Inner bark color.*—About 177B.

SHOOTS

Young shoot:
- *Form of tip.*—Fully open.
- *Distribution of anthocyanin coloration of tip.*—Piping (striped).
- *Intensity of anthocyanin coloration of tip.*—Medium.
- *Density of prostrate hairs on tip.*—Dense.
- *Density of erect hairs on tip.*—Absent.

Flowering shoot:
- *Vigor during flowering.*—Strong.
- *Attitude during flowering on shoots which are not tied.*—Semi-drooping.
- *Color of dorsal side of internodes.*—About Green 144A with Red 187A stripes.
- *Color of ventral side of internodes.*—About Green 144A.
- *Color of dorsal side of nodes.*—About Green 144A with Red 187A stripes.
- *Color of ventral side of nodes.*—About Green 144A.
- *Density of erect hairs on nodes.*—None.
- *Erect hairs on internode.*—Absent.
- *Density of prostrate hairs on nodes.*—Very sparse.
- *Density of prostrate hairs on internodes.*—Absent.
- *Anthocyanin coloration of buds.*—Absent.

Tendrils:
- *Distribution on the shoot at full flowering.*—Discontinuous.
- *Thickness.*—Medium.
- *Color.*—About 144A.
- *Form.*—Trifurcated.
- *Number of consecutive tendrils.*—Up to two.
- *Length of tendril.*—Long, about 32.1 cm.

LEAVES

Young leaves:
- *Color of upper surface of first 4 distal unfolded leaves.*—Green.
- *Average intensity of anthocyanin coloration of six distal leaves prior to flowering.*—Absent or very weak.
- *Density of prostrate hairs between veins at lower surface of 4th distal unfolded leaf.*—Absent.
- *Density of erect hairs between veins at lower surface of 4th distal unfolded leaf.*—Absent.
- *Density of prostrate hairs on veins at lower surface of 4th distal unfolded leaf.*—Medium.
- *Density of erect hairs on veins at lower surface of 4th distal unfolded leaf.*—Absent.

Mature leaves:
- *Average length.*—About 16.9 cm.
- *Average width.*—About 19.7 cm.
- *Size of blade.*—Large.
- *Shape of blade*—Pentagonal.
- *Number of lobes.*—5 to 7.
- *Anthocyanin coloration of main veins on the upper side of the blade.*—Absent.
- *Mature leaf profile.*—Undulate.
- *Blistering surface of blade upper surface.*—Medium.
- *Leaf blade tip.*—In the plane of the leaf.
- *Undulation of margin.*—Medium.
- *Apex.*—Cuspidate.
- *Thickness.*—Medium.
- *Undulation of blade between main and lateral veins.*—Only near petiole.
- *Shape of teeth.*—Both sides straight.
- *Length of teeth.*—Long.
- *Ratio length/width of teeth.*—Small.
- *General shape of petiole sinus.*—Wide open.
- *Tooth at petiole sinus.*—Absent.
- *Petiole sinus limited by veins.*—Absent.
- *Shape of upper lateral sinus.*—Lobes slightly overlapping.
- *Depth of upper lateral sinus.*—Medium to deep.
- *Density of prostrate hairs between veins on lower surface of blade.*—Absent.
- *Density of erect hairs between veins on lower surface of blade.*—Absent.
- *Density of prostrate hairs on main veins on lower surface of blade.*—Sparse.
- *Density of erect hairs on main veins on lower surface of blade.*—Sparse.
- *Density of prostrate hairs on main veins on upper surface of blade.*—Absent.
- *Autumn coloration of leaves.*—About 11B (color changes very late; typically frost kills leaves before color change occurs).

Upper surface:
- *Color.*—About 147A.
- *Surface texture.*—Rugose.
- *Surface appearance.*—Semi-glossy.
- *Goffering of blade.*—Absent.

Lower surface:
- *Color.*—About 147B.
- *Anthocyanin coloration of main veins on lower leaf surface.*—Absent.
- *Glossiness.*—Medium.
- *Pubescence.*—Absent.
- *Surface texture.*—Smooth.

Petiole:
- *Length of petiole.*—Long, about 12.8 cm.
- *Length of petiole compared to middle vein.*—Slightly shorter.
- *Density of prostrate hairs on petiole.*—None.
- *Density of erect hairs on petiole.*—None.
- *Shape of base of petiole sinus.*—V-shaped.

Woody shoot:
- *Shape.*—Stocky.
- *Internode length.*—Short, about 95.5 mm.
- *Width at node.*—13.2 mm.
- *Cross section.*—Circular.

*Surface.*—Striate.
*Main color.*—About Yellowish-Brown 166C.
*Lenticels.*—Absent.
*Density of erect hairs on nodes.*—None.
*Density of erect hairs on internodes.*—None.
*Growth of axillary shoots.*—Weak.

Buds:
*Shape.*—Slightly pointed.
*Size.*—Large.
*Position.*—Slightly held out.
*Cane bud fruitfulness.*—Basal fruitful.
*Time of bud burst.*—Late.

FLOWERS

General:
*Flower sex.*—Hermaphroditic.
*Length of first inflorescence.*—Long, about 21.4 cm.
*Position of first flowering node.*—$4^{th}$.
*Number of inflorescences per shoot*—1.1 to 2.
*Date of full bloom.*—May 5, 2000.
*Time of bloom.*—Late, as compared with similar varieties in the growing area of Wasco, Kern County, Calif.
*Size* (*diameter of fully open flower*)—Medium.

FRUIT

General:
*Ripening period.*—Late, about 60 days after the 'Thompson Seedless' variety.
*Use.*—Fresh market.
*Keeping quality.*—Good.
*Resistance.*—Insects: Medium. Diseases: Medium.
*Shipping quality.*—Good.
*Date of first harvest.*—Oct. 1, 2000.
*Solids-sugar.*—Medium (~18%).
*Refractometer test.*—18.8° brix.
*Acid.*—Low, about 39 g/L tartaric acid.
*Juice pH.*—3.90 on Oct. 13, 2000.

Cluster:
*Bunch size* (*peduncle excluded*).—Large.
*Bunch length* (*peduncle excluded*).—Long, about 21.9 cm.
*Bunch width.*—About 16.2 cm.
*Bunch weight.*—High, averaging about 775 g.
*Bunch density.*—Loose.
*Number of berries.*—About 208.
*Form.*—Conical.

Peduncle:
*Length of peduncle.*—Short to medium, about 4.8 cm.
*Lignification of peduncle.*—Strong.
*Color.*—About 144A.

Berry:
*Size.*—Medium.
*Uniformity of size.*—Uniform.
*Berry weight.*—Medium, about 3.93 g.
*Shape.*—Oblong.
*Presence of seeds.*—Rudimentary, about 3.17 mg/seed.
*Cross section.*—Circular.
*Dimensions.*—About 22.6 mm longitudinal axis by 17.4 mm horizontal axis.
*Skin color* (*without bloom*).—About Green-Yellow 145B.
*Coloration of flesh.*—Clear.
*Juiciness of flesh.*—Slightly juicy.
*Berry firmness.*—Firm.
*Particular flavor.*—None.
*Bloom* (*cuticular wax*).—Medium.
*Pedicel length.*—Intermediate, about 10.3 mm.
*Berry separation from pedicel.*—Difficult.
*Visibility of hilum.*—Slightly clear.
*Torus.*—Medium.

Skin:
*Thickness.*—Thin.
*Texture.*—Medium.
*Reticulation.*—Absent.
*Roughness.*—Absent.
*Tenacity.*—Tenacious to flesh.
*Tendency to crack.*—None.

Sugratwentytwo: Table of R.H.S. Color Codes:

| | | | R.H.S. Color Chart |
|---|---|---|---|
| VINE: | Trunk: | Inner bark color: | 177B |
| SHOOTS: | Flowering Shoot: | Dorsal side of internodes: | 144A with 187A stripes |
| | | Ventral side of internodes: | 144A |
| | | Dorsal side of nodes: | 144A with 187A stripes |
| | | Ventral side of nodes: | 144A |
| | Tendrils: | | 144A |
| LEAVES: | Mature Leaves: | Autumn of coloration leaves: | 11B |
| | Upper Surface: | | 147A |
| | Lower Surface: | | 147B |
| | Woody Shoot: | | 166C |
| FRUIT: | Peduncle: | | 144A |
| | Berry: | Skin color (without bloom): | 145B |

What is claimed is:

1. A new and distinct variety of grapevine cv. 'Sugratwentytwo' as herein illustrated and described.

* * * * *